United States Patent [19]

Higa et al.

[11] Patent Number: 4,902,716

[45] Date of Patent: Feb. 20, 1990

[54] ANTI-VIRAL CHAMIGRENE DERIVATIVES

[75] Inventors: Tatsuo Higa, Naha, Japan; Kenneth M. Snader, Vero Beach, Fla.

[73] Assignee: Harbor Branch Oceanographic Institutuion, Inc., Fort Pierce, Fla.

[21] Appl. No.: 682,896

[22] Filed: Dec. 18, 1984

[51] Int. Cl.$^4$ .................... A61K 31/12; A61K 35/80; C07C 49/597
[52] U.S. Cl. ................................ 514/546; 424/195.1; 514/691; 560/231; 560/248; 568/366; 568/377
[58] Field of Search ................ 514/546, 691; 560/231, 560/248; 568/366, 367; 424/195.1

[56] References Cited

U.S. PATENT DOCUMENTS

| | | | |
|---|---|---|---|
| 4,162,308 | 7/1979 | Calvin et al. | 514/546 |
| 4,162,309 | 7/1979 | Calvin et al. | 514/546 |
| 4,708,962 | 11/1987 | Higa et al. | 514/690 |

*Primary Examiner*—Werren B. Lone
*Attorney, Agent, or Firm*—Carroll F. Palmer

[57] ABSTRACT

This invention relates to antiviral compositions, a process for producing the compositions and a method for inhibiting viruses utilizing the compositions. More particularly, the compositions are halogenated chamigrenes extracted from sea hares which diet upon red algae.

15 Claims, No Drawings

ANTI-VIRAL CHAMIGRENE DERIVATIVES

FIELD OF THE INVENTION

This invention relates to new chamigrene derivatives which have useful antiviral activity. More particularly, this invention relates to chamigrene derivatives with antiviral activity which are derived from marine organisms, i.e., sea hares which diet upon red alga.

BACKGROUND OF THE INVENTION

Viral diseases inflict man, plants, insects, and animals. The prevention and control of viral diseases have important health and economic implications.

Viral diseases contribute to inflictions in humans including common colds, herpes and cancer and the importance of their control is obvious. Also important is control of viral diseases in animals for economic reasons as well as the ability of such animals to become virus reservoirs or carriers which facilitate the spreading of viral diseases to humans. Viral plant diseases disrupt the cultivation of fruit trees, tobacco, and various vegetables. Insect viral diseases are also of interest because of the insects' ability to transfer viral diseases to other hosts.

The prevention and control of viral diseases is thus of prime importance to man and considerable research has been devoted to antiviral measures. Certain methods and chemical compositions have been developed which aid in inhibiting, controlling or destroying viruses but new methods and antiviral chemical compositions are needed.

U.S. Pat. Nos. 4,162,308 and 4,162,309 to Calvin and Ellis describe that water soluble extract from marine red alga have been found to be effective to inhibit the growth of certain herpes viruses.

U.S. Pat. No. 4,162,308 describes water soluble attracts from marine red alga selected from a group consisting of *Turnerella mertensiana, Schizymenia epiphytica, Turnerella pennyi* algae and mixtures thereof as effective to inhibit the growth of herpes simplex virus, type 1 and type 2, and herpes zoster, and to relieve the pain caused by infection attributable to such viruses.

U.S. Pat. No. 4,162,309 describes the use of water soluble extracts from marine red alga selected from a group consisting of *Neodilsea americana* and *Neodilsea integra* algae and mixtures thereof to inhibit the growth of herpes simplex virus, type 1 and type 2, and herpes zoster, and to relieve the pain caused by infection attributable to such viruses. The entire disclosures of U.S. Pat. Nos. 4,162,308 and 4,162,309 are hereby incorporated herein by reference.

In addition to the water soluble red alga extracts described in the above noted U.S. patent applications to Calvin and Ellis other compounds have been isolated from red alga and marine organisms known as sea hares which are mollusks which diet on red algae. These compounds include halogenated chamigrenes and have been described in various literature references including P. J. Scheuer, Ed. *Marine Natural Products* Volume 1 (Martin) and Volume 5 (Erickson) Acedemic Press, 1978, 1983 the entire disclosure of this reference is hereby incorporated herein by reference. Halogenated chamigrenes have also been disclosed by Dr. Tatsuo Higa in a speech given in Japan in October of 1984, the entire disclosure of the Japanese abstract is hereby made of record and incorporated by reference, herein.

A co-pending application of the present inventors filed concurrently herewith relates to red alga extracts comprising certain cyclohexadienones which show antiviral activity.

It has now been found that certain chamigrene extracts from marine organisms such as sea hares which diet upon red alga, possess useful antiviral activity.

SUMMARY OF THE INVENTION

It is therefore an object of the invention to provide novel compositions which are useful as antiviral agents, and a process for producing such novel antiviral compositions.

It is an additional object of the invention to provide a method for inhibiting viruses, utilizing novel antiviral compositions.

Additional objects and advantages of the invention will be set forth, in part, in the description which follows and in part will be obvious from this description, or may be learned by the practice of the invention. The objects and advantages of the invention are realized and attained by means of the compositions, processes, methods, and the combinations particularly pointed out in the appended claims.

To achieve the objects in accordance with the purposes of the invention, as embodied and fully described here, the invention comprises a composition of the general formula (I):

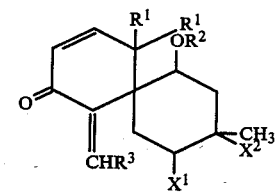

wherein both $R_1$ are the same and are hydrogen or a lower alkyl group, or $R_2$ is hydrogen, a lower alkyl or a lower acyl group, $R_3$ is hydrogen or a lower alkyl group, and $X_1$ and $X_2$ are the same or different and are a fluoro, chloro, bromo, iodo or lower alkoxy group.

In preferred embodiments of the invention, the lower alkyl and acyl groups have from 1 to 5 carbon atoms and $X_1$ and $X_2$ are the same or different and are a chloro or bromo group.

In a more preferred embodiment of the invention, the invention comprises a composition of the formula

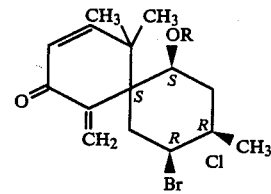

wherein R is H or

As embodied and fully described herein, the invention also comprises an antiviral composition comprising, as active ingredient, an effective antiviral amount of one or more of the compositions according to Formula I or preferably Formula II and a non-toxic pharmaceutically acceptable carrier or diluent.

As embodied and broadly described herein, the invention also comprises a process to produce the compound of formula II comprising the steps of: collecting a digestive gland from a sea hare, *Aplysia dactylomela*, which diet on red alga genus Laurencia; contacting the digestive gland with a suitable polar organic solvent to obtain a first extract; admixing the first extract with a second suitable hydrocarbon solvent to form a second solvent extract; removing the second solvent extract; and isolating the compound from either the second solvent extract by chromatography from this step or after an intermediary saponification step. Preferably, the first solvent is acetone and the second solvent is hexane.

As embodied and fully described herein, the invention also comprises a method for inhibiting viruses comprising contacting a virus with an effective antiviral amount of one or more compositions of formula I or preferably formula II.

It is to be understood that both the foregoing general and the following detailed description are examplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following example section.

In accordance with the invention, a composition of the formula:

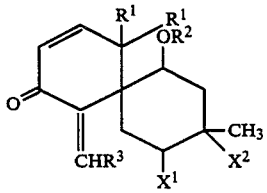

I wherein both R₁ groups are the same and are hydrogen or a lower alkyl group, R₂ is hydrogen, a lower alkyl or a lower acyl group, R₃ is hydrogen or a lower alkyl group, and X₁ and X₂ are the same or different and are a fluoro, chloro, bromo, iodo or lower alkoxy group. Preferably, the lower alkyl and acyl groups have from 1 to 5 carbon atoms, more preferably from 1 to 3 carbon atoms, and most preferably, the lower alkyl and acyl groups have a single carbon atom.

Preferably, X₁ and X₂ are the same or different and are a chloro or bromo group. More preferably, X₁ is a bromo and X₂ is a chloro group. More particularly, preferred embodiments of the invention comprise compositions of the structures III and IV as indicated below:

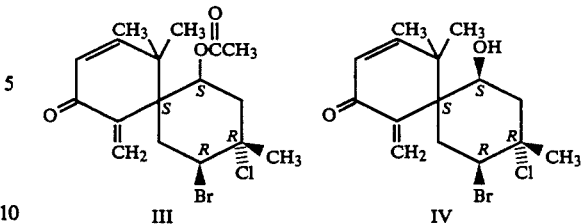

In accordance with the invention an antiviral composition is provided comprising as active ingredients an effective antiviral amount of one or more of the compositions described above and identified by formulas I–IV and a non-toxic pharmaceutically acceptable carrier or diluent. While effective amounts may vary, as conditions in which the antiviral compositions are used vary, a minimal dosage required for activity is generally between 50 and 200 micrograms against 25 to 80 plaque-forming units of virus cells. Useful non-toxic pharmaceutically acceptable carrier or diluents include, but are not limited to, the following: ethanol, dimethyl sulfoxide, and glycerol.

In accordance with the invention, a process to produce the compound of Formula III comprises the steps of collecting a digestive gland from a sea hare, genus and species *Aplysia dactylomela*, which have been dieting upon red algae, genus Laurencia. The digestive glands are surgically removed from the individual sea hares. The digestive glands are then contacted with acetone to obtain an acetone extract from the digestive gland and its contents. The acetone extract is then concentrated by evaporation facilitated, for example, by gentle heating or reduced pressure. The concentrated extract is admixed with hexane to form a new hexane extract. The hexane extract is removed and concentrated and a compound according to Formula III is isolated by chromatography. Any suitable chromatography technique may be used, but it has been found that silica gel chromatography utilizing a Lobar column (Si-60) will yield a purified product after several chromatography runs.

While acetone and hexane are the present first and second solvents, respectively, of choice acetone may be replaced with another suitable polar organic solvent (e.g. methyl ethyl ketone, methyl isobutyl ketone, or ethyl acetate) and hexane may be replaced with another suitable hydrocarbon solvent which is capable of extracting the products (e.g. pentane, hexane, or heptane).

The compound according to Formula IV is obtained according to the process of the invention by following the steps outlined above for producing the compound of Formula III and subjecting compound III to saponification with, for example, a 0.1% solution of potassium hydroxide in ethanol.

In accordance with the present invention, virus cells are inhibited in their growth or killed by a method comprising contacting a virus with an effective antiviral amount of one or more compositions according to Formulas I–IV. The effective amount as stated above is generally from 50 to 200 micrograms for every 25 to 80 plaque-forming units of virus cells. The compound of formulas I–IV are active for inhibiting or killing a diverse range of viruses including, but not limited to, RNA viruses, vesicular stomatitis (herein "VSV") adeno-, corona-, reo- and influenza viruses and the DNA virus, Herpes Simplex—I and II (herein "HSV-I" and "HSV-II") adeno- and papova-viruses.

These results indicate that the compositions of Formulas I–IV should also be useful in controlling viral infections in host animals and plants which are caused by the virus which is thus inhibited or destroyed. Viral infections which may be controlled by utilizing the compositions of the present invention include, but are not limited to, those caused by RNA virus such as arena virus, corona viruses and influenza virus, and viral infections caused by the DNA viruses, such as adeno virus and vaccinia virus. The invention may also be useful in controlling common viral infections of plants.

It is therefore apparent that the compositions of the invention, the processes for producing the compositions of the invention and the methods for utilizing the compositions of the invention to inhibit viruses are effective for inhibiting or destroying viruses and therefore controlling viral diseases caused by such viruses in fulfillment of the objects of the invention.

EXAMPLES

The invention will now be illustrated by examples. The examples are not intended to be limiting of the scope of the present invention. In conjunction with the detailed and general description above, the examples provide further understanding of the present invention and outline a process for producing compositions of the invention.

The following examples represent preferred embodiments of the compositions, processes and methods of the invention. The starting materials and reagents in the examples whose method of preparation are not indicated, are commercially available from sources known to the art such as chemical supply houses.

EXAMPLE 1

Preparation of:

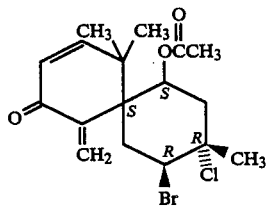

III 6 individual sea hares (a mollusk *Aplysia doctylomela*) (approximately 360 grams each) were collected at Miyako Island, Okinawa where they were observed to be dieting upon red algae genus Laurencia the sea hares (*Aplysia doctylomela*) have a single digestive gland. The digestive glands of the sea hares were removed and collected (about 115 gms total). The glands were placed in a suitable vessel and 300 ml. of acetone was added to the vessel and the mixture was homogenized to produce a slurry.

The slurry was filtered to provide an acetone extract and this was extracted twice more with 300 ml. of acetone. The acetone extract was concentrated under vacuum at room temperature. The concentrated acetone extract yielded an aqueous suspension which was admixed with 300 ml. of hexane in a separatory funnel. The hexane fraction was extracted for a total of three times with 300 ml. fractions of hexane and the hexane removed to yield 3.8 gms of crude product oil.

The hexane extract was subjected to chromatographic separation by repeated runs through a Silica gel packed column with a 3:1 hexane/chloroform eluent. The product was then subjected to additional chromatographic purification in a $SiO_2$ Lobar column (Si-60) to yield 1.1 grams of the compound of Formula III with a melting point in the range of 105° to 106° C.; $[\alpha]_D^{20} -27.8°$ ($C_{0.54}$ $CHCl_3$); and $C_{17}H_{17}$, $Br_1$, $Cl_1$, $O_3$ by combustion analysis.

EXAMPLE 2

Preparation of:

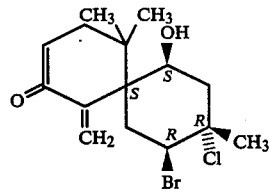

IV

The steps of Example 1 were repeated to yield the compound of Formula III which was saponified to the compound of Formula IV according to the following steps.

The compound of Formula III was admixed with a 0.1% KOH in ethanol solution and subjected to gentle stirring at room temperature to yield the compound of Formula IV.

The compound of Formula IV was isolated and purified by chromatographic separation as in Example 1 to yield the Formula IV product with a melting point range of 174° to 176° C. Approximately 70% of ether byproduct of the formula V:

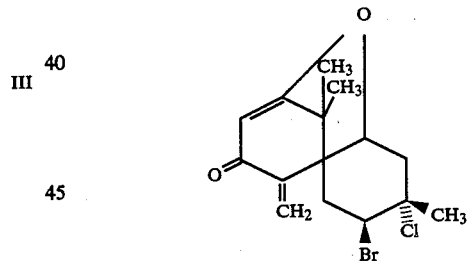

V was also produced (melting point range of 144° to 145° C.).

ANTIVIRAL ACTIVITY OF THE COMPOUNDS OF THE INVENTION

The following assay method was utilized to illustrate the antiviral effectiveness of the compounds of formulae III and IV:

Day 1:
(1) Remove 75 cm² culture flasks from incubator (these were plated the previous week).
(2) Aspirate medium.
(3) Wash with 10 ml. PBSA or Puck's Saline.
(4) Aspirate.
(5) Wash a second time with 10 mL PBSA or Puck's Saline.
(6) Aspirate.
(7) Add 2 ml. trypsin/EDTA. Incubate until cells detach (10–20 min).

(8) Once detached, shake vigorously and immediately add 8 ml. medium and shake again.

(9) Count cells. (To 0.5 ml. cell suspension add 0.1 ml. trypan blue. Wait 5-10 minutes. Count 4 corner squares and middle square of 5×5 array in hemocytometer. Blue cells are dead. Total count per 10 ml. in culture flask = number of live cells × 6 × $10^5$).

(10) Maintain cell line by adding 3 × $10^6$ cells to another 75 $cm^2$ culture flask. Bring to 30 ml. with fresh medium.

(11) For assay, add 1 × $10^6$ cells to each well (6 wells per culture dish). Bring each well to 2 ml. with fresh medium.

(12) Incubate overnight at 37° C.

Day 2:
(1) Aspirate medium.
(2) Add 0.5 of medium containing 200 pfu HSV-I.
(3) Incubate 102 hr with a small amount of shaking.
(4) Add 2 ml. MC-4000 to each well.
(5) Place disks on surface and wash through (1 mg/disc, 0.5 mg/disc, 0.25 mg/disc, etc. for crude extracts).
(6) Incubate 48 hr. (making sure dishes remain level).

Day 4:
(1) Add 2 ml. neutral red medium.
(2) Incubate overnight.

Day 5:
(1) Read wells, e.g. 26 (++) where 26 indicates zone of cytotoxicity as the diameter in mm (12.5 mm to 36 mm) and (++) indicates the inhibition of plaque formation: complete inhibition (+++); a few plaques around the outside of well (++); definite inhibition (+); questionable inhibition (+/−); no inhibition (−); and no conclusion due to complete cytotoxicity.

Day 7:
Begin cycle at Day 1.

II RECIPES

CULTURE MEDIUM
1 L GIBCO MEM (plus non-essential a.a.'s with Earle's Salts).
2.2 gms. $NaHCO_3$
50 ml. calf serum
105 units penicillin
50 mg streptomycin MC-4000
500 ml. Culture Medium made to half volume (twice as concentrated)
500 ml. 2% v/w 4000 cps methyl cellulose NEUTRAL RED MEDIUM
(ALWAYS MAKE FRESH)
500 ml. CULTURE MEDIUM made to half volume (twice as concentrated)
500 ml. 4% v/w 15 cps methyl cellulose
100 mg neutral red from stock solution PUCK'S G SALINE SOLUTION
to 1 L distilled $H_2O$ add:
8.00 g NaCl
0.40 g KCl
0.15 g $KH_2PO_4$
0.29 g $Na_2HPO_4.7H_2O$
2.0 ml. 1% phenol red
1.10 g glucose
autoclave TRYPSIN-EDTA
for 1 L:
"dissolve" 2 g DIFCO 1-250 trypsin plus 0.2 g EDTA in 100 ml.
Puck's Saline.
sterile filter.
add to 900 ml. sterile Puck's Saline.

PBSA
to 1 L distilled $H_2O$ Add:
8.00 G NaCl
0.20 g KCl
1.50 g $Na_2HPO_4.7H_2O$
0.25 g $KH_2PO_4$
autoclave The following antiviral inhibiting activity results were obtained utilizing the compounds of Formula III and IV at Day 5:

| Runs | Compound | Amount Micrograms | Cytotoxicity | HSV-1 activity | VSV activity |
|------|----------|-------------------|--------------|----------------|--------------|
| 1 | III | 400 | 10 mm | + | ++ |
| 2 | III | 200 | 0 mm | + | ++ |
| 3 | III | 100 | 0 mm | +− | + |
| 4 | III | 50 | 0 mm | 0 | +− |
| 5 | IV | 400 | 12 mm | + | ++ |
| 6 | IV | 200 | 0 mm | + | ++ |
| 7 | IV | 100 | 0 mm | 0 | + |

The scope of the present invention is not limited by the description, examples, and suggested uses herein and modification can be made without departing from the spirit of the invention. For example, it may be noted that other derivatives of the chamigrene of examples 1 and 2 such as, a fluorinated chamigrene may possess useful antiviral activity analagous to those preferred embodiments described above. Further, the compositions as claimed herein may have other useful applications such as, for example, analgesic applications. Thus, it is intended that the present invention cover the modifications and variations of this invention provided that they come within the scope of the appended claims and their equivalents.

What is claimed is:

1. A composition of the general formula:

wherein both $R^1$ groups are the same and are hydrogen or a lower alkyl group $R^2$ is hydrogen, lower alkyl or a lower acyl group, $R^3$ is hydrogen or a lower alkyl group, and $X^1$ and $X^2$ are the same or different and are a fluoro, chloro, bromo, iodo or lower alkoxy group.

2. A composition according to claim 1 wherein the lower alkyl and acyl groups have from 1 to 5 carbon atoms.

3. A composition according to claim 1 wherein the lower alkyl and acyl groups have from 1 to 3 carbon atoms.

4. A composition according to claim 1 wherein the lower alkyl and acyl groups have a single carbon atom.

5. A composition according to claim 1 wherein $X^1$ and $X^2$ are the same or different and are a chloro or bromo group.

6. A composition of the formula:

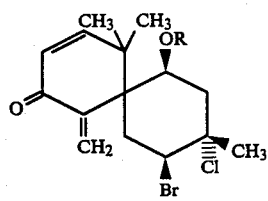

wherein R is H or

7. A composition according to claim 6 wherein R is

8. A composition according to claim 6 wherein R is H.

9. An antiviral composition comprising, as active ingredient, an effective antiviral amount of one or more of the compositions of claim 1 and a non-toxic pharmaceutically acceptable carrier or diluent.

10. An antiviral composition comprising, as active ingredient, an effective antiviral amount of one or more of the compositions of claim 6 and a non-toxic pharmaceutically acceptable carrier or diluent.

11. A process to produce a composition according to claim 7 comprising the steps of:
collecting a digestive gland from a sea hare, *Aplysia dactylomela*, which diets on red alga genus Laurencia;
contacting said digestive gland with a first polar organic solvent selected from the group consisting of acetone, methyl ethyl ketone, methyl isobutyl ketone and ethyl acetate to obtain a first extract comprising a composition according to claim 7;
admixing the first extract with a second hydrocarbon solvent to form a second solvent extract;
removing the second solvent extract; and
isolating by chromatography the composition of claim 7 from the second extract.

12. A process according to claim 11 wherein the first solvent is acetone and the second solvent is hexane.

13. A process to produce a composition according to claim 8 comprising the steps of:
collecting the digestive gland from a sea hare, *Aplysia dactylomela*, which diets or red alga genus Laurencia;
contacting said digestive gland with acetone to obtain an acetone extract comprising a composition of formula Z

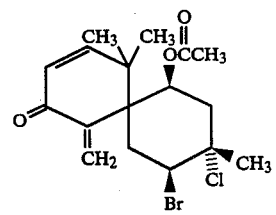

admixing the acetone extract with hexane to form a hexane extract;
removing the hexane extract;
isolating by chromatography the composition Z from the hexane extract;
saponifying said composition Z with an aqueous alkali solution; and
isolating the composition of claim 8 by extraction with ethanol.

14. A method for inhibiting viruses in a host comprising contacting a virus with an effective antiviral amount of one or more compositions of claim 1.

15. A method for inhibiting viruses in a host comprising contacting a virus with an effective antiviral amount of one or more compositions of claim 6.

* * * * *

UNITED STATES PATENT AND TRADEMARK OFFICE
CERTIFICATE OF CORRECTION

PATENT NO. : 4,902,716

DATED : February 20, 1990

INVENTOR(S) : Tatsuo Higa, Kenneth M. Snader

It is certified that error appears in the above-identified patent and that said Letters Patent is hereby corrected as shown below:

Column 2:  lines 51-59:  should read

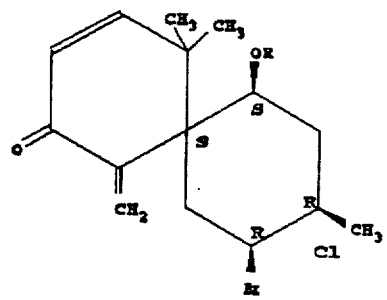 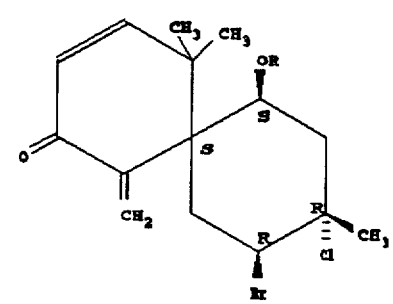

Column 7:  line 20: "wash" should read --push--.

Signed and Sealed this

Fourteenth Day of January, 1992

*Attest:*

HARRY F. MANBECK, JR.

*Attesting Officer*  *Commissioner of Patents and Trademarks*